United States Patent [19]

Gould et al.

[11] Patent Number: 4,496,535

[45] Date of Patent: Jan. 29, 1985

[54] POLYURETHANE POLYENE COMPOSITIONS

[75] Inventors: Francis E. Gould, Princeton; Christian W. Johnston, Neshanic Station, both of N.J.

[73] Assignee: Tyndale Plains-Hunter, Ltd., Princeton, N.J.

[21] Appl. No.: 607,676

[22] Filed: May 7, 1984

Related U.S. Application Data

[60] Division of Ser. No. 433,481, Oct. 8, 1982, Pat. No. 4,454,309, which is a continuation-in-part of Ser. No. 206,407, Nov. 12, 1980, Pat. No. 4,359,558.

[51] Int. Cl.$^3$ .............................. B32B 1/08; A61J 3/06; A61J 3/00
[52] U.S. Cl. .................................. 424/19; 351/160 H; 428/36; 428/423.1; 428/343; 424/28
[58] Field of Search ................. 525/28, 454, 455, 539, 525/920, 937; 528/75, 904; 424/28, 16, 19; 204/159.13; 428/36, 907, 423.1, 343; 351/160 H

[56] References Cited

U.S. PATENT DOCUMENTS

| | | | |
|---|---|---|---|
| 3,297,745 | 1/1967 | Fekete et al. | 525/920 |
| 3,553,174 | 1/1971 | Hausslein et al. | 528/50 |
| 3,719,638 | 3/1973 | Huemmer et al. | 525/293 |
| 3,822,238 | 7/1974 | Blair et al. | 528/904 |
| 3,931,123 | 1/1976 | Vacik et al. | 521/905 |
| 3,975,350 | 8/1976 | Hudgin et al. | 521/905 |
| 4,056,496 | 11/1977 | Mancini et al. | 521/905 |
| 4,116,786 | 9/1978 | Hodakowski | 204/159.13 |
| 4,117,184 | 9/1978 | Erickson et al. | 521/905 |
| 4,209,605 | 6/1980 | Hoy et al. | 528/54 |
| 4,246,391 | 1/1981 | Watson | 528/49 |
| 4,250,248 | 2/1981 | Faust | 525/127 |
| 4,359,558 | 11/1982 | Gould et al. | 525/454 |
| 4,454,309 | 6/1984 | Gould et al. | 525/454 |

*Primary Examiner*—Alexander S. Thomas
*Attorney, Agent, or Firm*—George F. Mueller

[57] ABSTRACT

Shaped three-dimensional structures formed of polyurethane polyene compositions obtained by reacting from about 10 to about 50 parts by weight of a polyene in the presence of about 100 parts by weight of a hydrophilic polyurethane resin. The resulting products will swell and increase in weight upon immersion in water and are permeable to gases, moisture vapor, ions, and other low molecular weight species. The hydrophilic polyurethane polyene compositions may be molded to form shaped products that are dimensionally stable after repeated exposure to boiling water and exhibit memory.

23 Claims, No Drawings

POLYURETHANE POLYENE COMPOSITIONS

This application is a division of Ser. No. 433,481, filed Oct. 8, 1982 U.S. Pat. No. 4,454,309, which is a continuation-in-part of application Ser. No. 206,407, filed Nov. 12, 1980 U.S. Pat. No. 4,359,558.

This invention relates to hydrophilic polyurethane polyene compositions. More particularly, the present invention relates to compositions obtained by the reaction of one or more polyenes in the presence of one or more hydrophilic polyurethanes that may be obtained by the reaction of a polyalkylene glycol with a diisocyanate.

The hydrophilic polyurethane polyene compositions of the present invention are insoluble in methanol, will form a hydrogel upon immersion in water, are permeable to gases, ions, moisture vapor and other low molecular weight species, are dimensionally stable, even in the presence of boiling water, and exhibit memory.

The hydrophilic polyurethane polyene compositions of the present invention may be prepared by reacting a polyene selected from the group consisting of polyallyl esters having the formula:

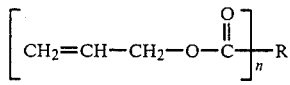

wherein n is a whole number larger than 1 and smaller than 4, and R is the residue of a polybasic acid; and polyacrylic esters having the formula:

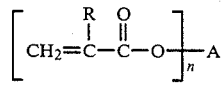

wherein n is a whole number larger than 2 and smaller than 7, R is hydrogen or a methyl radical and A is the residue of a polyhydric alcohol; in the presence of a hydrophilic polyurethane. A free radical catalyst is present to initiate the reaction of the polyene.

The hydrophilic polyurethanes that are employed as one component of the present invention may be made by the reaction of:
(A) one or more diols having a number average molecular weight in the range of from about 200 to 20,000, selected from the group consisting of:
  (a) diethylene glycol, and
  (b) long-chain polyoxyethylene diols, with
(B) a urethane precursor selected from the group consisting of organic polyisocyanates and nitrile carbonates in the presence of an organic tin catalyst. If desired, a polyfunctional lactone having the formula:

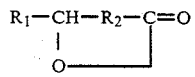

wherein $R_1$ is a monovalent radical selected from the group consisting of —H, —$CH_2NH_2$, —$SO_2CH_3$, —CHOHCOOH, and —$(CHOH)_nCH_2OH$; n being an integer from 0 to 5; and $R_2$ is a divalent radical —$(CHOH)_m$—; m being an integer from 2 to 10; may be added in amounts of from 0.1% to 25% of the weight of the total reaction mixture. Polyurethane resins containing such polyfunctional lactones are described in U.S. Pat. Nos. 4,156,066 and 4,156,067.

The hydrophilic polyurethane component which is present with the polyene at the time of its reaction contains polyoxyethylene glycols (diols) having the formula:

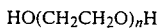

wherein n is a whole number larger than 1 and smaller than about 182. Diethylene glycol may be present and the long-chain, water-soluble diols should have a molecular weight of at least about 200 and preferably 1450 to 7500. Suitable diols consist predominantly of oxyethylene groups, though a minor proportion of oxypropylene groups may be included.

The polyisocyanate used to make the first component of the present invention may be represented by $R(NCO)_n$ wherein n is greater than 1, preferably 2–4, and R is an aliphatic, alicyclic, aliphatic-alicyclic, aromatic, aliphatic-aromatic or alicyclic aromatic hydrocarbon compound of from 4 to 26 carbon atoms, but more conventionally from 6 to 20 and generally from 6 to 13 carbon atoms. Representative examples of the above isocyanates are: hexamethylene diisocyanate; trimethylhexamethylene diisocyanate; dimer acid diisocyanate; isophorone diisocyanate; diethylbenzene diisocyanate; decamethylene 1,10-diisocyanate; cyclohexylene 1,2-diisocyanate and cyclohexylene 1,4-diisocyanate and the aromatic isocyanates such as 2,4- and 2,6-tolylene diisocyanate; 4,4-diphenylmethane diisocyanate; 1,5-naphthalene diisocyanate; dianisidine diisocyanate; tolidine diisocyanate; a polymeric polyisocyanate such as neopentyl tetra isocyanate; m-xylylene diisocyanate; tetrahydronaphthalene-1,5 diisocyanate; and bis(4-isocyanatophenyl) methane.

The preferred isocyanate is methylene di(cyclohexyl isocyanate). Another but slightly less preferred diisocyanate is isophorone diisocyanate.

Other compounds which are useful are the isocyanate equivalents which produce the urethane linkages such as the nitrile carbonate, that is, the adiponitrile carbonate of the formula:

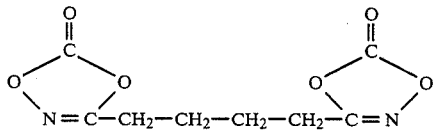

In the manufacture of the hydrophilic polyurethane resin component of this invention, low molecular weight polyethylene glycols and diethylene glycol may be used. Minor amounts of dipropylene glycol or an aromatic glycol may be added to the reaction mixture. The preferred low molecular weight aromatic polyols are bisphenol-A and 4,4'-sulfonyldiphenol.

The proportions in which the long-chain polyglycol and the low molecular weight glycol, that is, diethylene glycol are present in the hydrophilic polyurethane component of this invention depends on the hydrophobic-hydrophilic balance present in each and desired in the final composition. Increasing the molecular weight of the long-chain polyoxyethylene glycol and/or the amount of this polyol contributes strong hydrophilic properties to the final product. This effect may be counterbalanced by increasing the proportion of low molecular weight glycol, that is, diethylene glycol or dipropylene glycol.

Keeping the above in mind (that it is the number polyethylene oxide groups in the polymer molecular that determines hydrophilic properties and that the polypropylene oxide groups are hydrophobic), it is a simple matter to choose mixtures of reactants such that the hydrophilic polyurethane to be present at the time of reacting the polyene will have the desired properties. By choosing the molecular weight of the polyethylene glycol or using two polyalkylene glycols of different molecular weight, one may "tailor make" the hydrophilic polyurethane component to satisfy a wide range of properties. It will be understood that the term "hydrophilic polyurethanes" as used throughout the specification and claims is used to describe polyurethanes which when immersed in water will swell and absorb from about 20% up to about 500% of their weight of water without change in physical or chemical composition. Moreover, the hydrophilic polyurethane polyene compositions of the present invention, like the hydrophilic polyurethane component also will absorb water when immersed therein and take up at least 20 weight percent water.

As mentioned above, the hydrophilic polyurethane component that is reacted with one or more polyenes to form the compositions of the present invention may contain a polyfunctional lactone. Representative examples of the polyfunctional lactones are those derived from polysaccharides and monosaccharides such as mannolactone, delta gluconolactone, sorbolactone and D-glucuronolactone.

It is desirable that the lactones employed have at least 3 and preferably 4 or more hydroxyl groups in the molecule or at least 1 more than is required to form a linear polyurethane chain. These free (unreacted) hydroxyl groups remain in the polymer backbone and are available for crosslinking the polymer. The lactone ring is also reactive and must be opened, that is, by hydrolysis, to solubilize the polyurethane component in alcohol.

In making the first component of the present invention, the glycols are mixed with the lactone, if present, and the polyisocyanate is reacted with the mixture although other techniques may be used. The reaction is catalyzed by known catalyst for such reaction, suitable ones being tin salts and organic tin esters such as dibutyl tin dilaurate, tertiary amines such as triethyl diamine (DABCD), N,N,N',N'-tetramethyl-1,3-butane diamine and other recognized catalyst for urethane reactions which are well known in the art. The reaction can be conducted in the absence or presence of diluent or solvent. If a lactone is present, the first component is treated with caustic to obtain alcohol solubility.

The second component of the composition of the present invention is a polyene which may be a polyacrylate obtained by reacting acrylic acid chloride (propenoyl chloride) or methacrylic acid chloride (2-methyl propenoyl chloride) with a polyhydric alcohol. The preferred polyacrylates are the triacrylate and trimethacrylates of trimethylol propane although the polyacrylates and polymethacrylates of pentaerythritol may be used as the second component. Such acrylic esters may be represented by the formula:

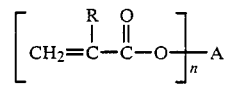

wherein n is a whole number larger than 2 and smaller than 7, R is hydrogen or a methyl radical, and A is the residue of a polyhydric alcohol.

The polyene that is used as the second component of the present invention may also be a polyallyl ester of a polybasic acid. The preferred polyallyl esters are diallyl phthalate and diallyl terephthalate although other polyallyl esters of polybasic acids such as m-phthalic, carbonic, glycolic, succinic, oxalic maleic, maleic malonic, adipic and tribasic carboxylic acids are suitable. Such polyallyl esters may be represented by the formula:

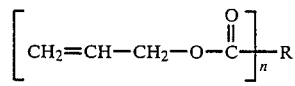

wherein n is a whole number larger than 1 and smaller than 4, and R is the residue of a polybasic acid.

In preparing the hydrophilic polyurethane polyene composition of the present invention, 100 parts by weight of one or more polyurethanes are dissolved together with from about 10 to about 50 parts of one or more polyenes in a solvent such as methanol or 95% ethanol and a free radical catalyst is added to initiate polymerization of the polyene. The solution of the two components may be cast to form a film and heat cured at temperatures in the range of 110° C. to 135° C. or alternatively, the cast film may be cured by the action of ultraviolet light. If insolubilization of the two component composition is to be initiated by ultraviolet light, it is not necessary that the free radical catalyst be present. It may be desirable, however, to add an ultraviolet absorber such as Rhodamine B or an azo type catalyst such as azobisisobutrylnitrile to the mixture of the two components.

If it is desired to prepare shaped articles or tubing from the hydrophilic polyurethane polyene compositions of the present invention, the solvent may be removed under reduced pressure and the residual mixture can be molded at temperatures of 110° C. to 135° C. for from about 2 to about 20 minutes to cure and insolubilize the hydrophilic polyurethane diacrylate composition.

The hydrophilic polyurethane polyene compositions of the present invention are dimensionally stable upon repeated exposure to boiling water and have unique physical properties that are of advantage when used in the manufacture of soft contact lens.

The above described hydrophilic polyurethane polyene resin compositions are also useful as coatings, molding compounds, absorbents, controlled release agents, ion exchange resins, and in the manufacture of dialysis membranes, dentures, cannulae, contact lenses, packaging components, burn dressings, contraceptive devices, sutures, surgical implants, blood oxygenators, intrauterine devices, vascular prostheses, oral delivery systems, battery separator plates, eye bandages, corneal prostheses, antifog coatings, surgical drapes, oxygen exchange membranes, artificial finger nails, finger cots, adhesives, gas permeable membranes, and in protective and drag resistant coatings.

The practice of the invention is further illustrated by the following examples without being restricted thereto, the parts being by weight unless otherwise stated.

EXAMPLE I

A polyurethane polymer is prepared by melting together and stirring in a container 822.3 parts of CARBOWAX 8000 ® (a polyethylene glycol having a number average molecular weight of 7,500–8,000 manufactured by Union Carbide Corporation, New York, N.Y. 10017), 23.0 parts of diethylene glycol and 5.4 parts of water. The mixture becomes clear at about 80° C., and is cooled to 75° C. When the temperature reaches 75° C., 149.7 parts of methylene bis-cyclohexyl-4,4'-isocyanate (a product identified as DESMODUR W ® by the Mobay Chemical Corporation, Penn Lincoln Parkway West, Pittsburgh, Pa. 15205) is added with stirring. The mixture is stirred at 75° C. until homogeneous, cooled to 50° C. and then there is added 2.0 parts by volume of an organic tin catalyst solution, dibutyl tin dilaurate (a product identified at $T_{12}$ (manufactured by Metal and Thermite Company of Rahway, N.J.). The catalyst is added and the reaction mixture is allowed to exotherm from 50° C. to 75° C. The molten product is poured at a temperature of 75° C. into teflon coated polypropylene pans and heated in an oven at 100° C. to complete the reaction and form a foamed hydrophilic polyurethane product.

The polyurethane foam is cooled to room temperature, removed from the pans and dissolved in 95% ethanol to give a solution containing 9.82% by weight solids. To 305.5 parts of this polyurethane solution in ethanol (30 g solids) is added with stirring 4.5 parts of trimethylol propane triacrylate and 0.328 parts of isobutyl peroxy octoate. The solvent is evaporated at room temperature under vacuum to give a product comprising 100 parts of hydrophilic polyurethane and 15 parts of trimethylol triacrylate that is subsequently molded in the shape of a contact lens at 125° C. for 30 minutes. The product is dimensionally stable and may be repeatedly boiled in water and cooled to room temperature without any perceptible change in its nature. The product increases in size and picks up about 255 weight percent water when swelled in water. If this product is boiled in water and cooled, it will be found to have picked up about 500 weight percent water. Upon subsequent boiling and cooling, the weight gain remains about 500% by weight. This product exhibits elastic memory as it may be compressed into a different shape in a press at elevated temperatures and permitted to cool. When placed in water, it will revert to its original lens shape. It was determined that this product, after it was cured under heat and pressure, would take up 251% to 258% water and exhibited 40% to 50% elongation.

EXAMPLE II

A contact lens may be prepared by spinning from solution. The solution of hydrophilic polyurethane with trimethylol triacrylate dissolved in alcohol described in Example I above, is evaporated under vacuum, to increase the solids content, until the viscosity reaches 12–15 poise (approximately 11–12% non-volatile).

A concave mold conforming to the desired shape of the air side of a contact lens is mounted on a vertical shaft that can be rotated at a top speed of 200 rpm.

The concave portion of the mold is half filled with the above solution. The mold slowly started and brought to top speed in 5 minutes. It is allowed to spin at top speed for an additional 5 minutes. The spinning mold is allowed to come to rest.

The mold is then placed in an oven flooded with nitrogen. The temperature is allowed to rise slowly to 135° C. and is maintained for 15 minutes.

After cooling, the mold is placed in water and the polymer hydrates and becomes separated from the mold.

EXAMPLE III

A polyurethane resin is prepared as described above in Example I from the following compounds:

| Polyethylene glycol (m. wt. 1450) | 1232 parts |
|---|---|
| Diethylene glycol | 134 parts |
| Water | 6 parts |
| DESMODUR W ® | 628 parts |

Three parts by volume of a stannous octoate catalyst identified as $T_9$ by the Metal and Thermite Company of Rahway, N.J. is added to the stirred reaction mixture at a temperature of 50° C. The temperature initially rises at a slow rate and then more rapidly. When the temperature reaches 85° C., the reaction mass is poured into teflon coated pans, placed in an oven with forced air circulation at 100° C. for 30 minutes and then cooled to room temperature.

One hundred parts of the foamed polyurethane is dissolved in 900 parts of 95% ethanol and 30 parts of trimethylol propane triacrylate and 2.4 parts of tertiary-butyl-peroctoate are added with thorough mixing. The solvent is removed at room temperature to produce a white plastic mass that is somewhat sticky when first prepared.

The plastic mass is placed in a mold and molded at 135° C. for 20 minutes to give a cured (crosslinked) hydrophilic polymer having application in the manufacture of soft contact lens.

If desired, the polyurethane-polyene composition described above in this Example may be mixed with, or used to encapsulate drugs prior to the curing step. The cured polymer will slowly release the drug when placed in an aqueous or saline solution or in body fluids. The resin composition described in this Example, therefore, may be formed into any convenient shape, that is, tablets for oral ingestion, implants, and suppositories to provide a controlled release of the drug.

EXAMPLE IV

A hydroxyl terminated polyurethane resin is prepared by the method described in Example I above from the following reaction mixture:

| Polyethylene glycol (m. wt. 1450) | 977 parts |
|---|---|
| Diethylene glycol | 211 parts |
| DESMODUR W ® | 807 parts |
| Stannous octoate | 1.3 parts |

One hundred parts of the polyurethane polymer is modified with 25 parts of diallyl phthalate by dissolving both components in 95% ethanol and curing in the presence of 2 parts of tertiary butyl peroctoate as described above in Example III.

The cured polyurethane-polyene composition is more rigid than that prepared in Example III above. It is pressed into the form of a flat sheet by heating under pressure in a press at 100° C. and increasing the temperature to 130° C. for 2 minutes while maintaining the pressure. The sheet may be used as a membrane for water and vapor transmissions and has medicinal applications as permeable dressings, etc. It is particularly advantageous as a burn dressing into which medicaments such as sulfadiazine may be incorporated. The polyurethane-polyene composition is useful as a dialysis membrane and finds application in separation techniques.

EXAMPLE V

A polyurethane resin is made by the method described in Example I above from the following reaction mixture:

| | |
|---|---|
| Polyethylene glycol (m. wt. 7500) | 1644 parts |
| Diethylene glycol | 46 parts |
| Water | 10 parts |
| DESMODUR W ® | 300 parts |
| Dibutyl tin dilaurate | 3 parts |

The temperature of the reaction mixture increases to 85° C. during the exotherm, at which time the mixture is poured into 11 cm×24 cm teflon coated baking tins and heated in an oven for 1 hour at 100° C.

The polyurethane polymer is cooled to room temperature and modified with diallyl phthalate by adding to 100 parts of the polyurethane dissolved in 900 parts of 95% ethanol, 15 parts of diallyl phthalate and 1.2 parts of tertiary-butyl-peroctoate. The alcohol is removed under vacuum and the mixture is cured in an oven for 15 minutes at 150° C.

This polyurethane-diallyl phthalate composition shows a 332 percent increase in weight after being immersed in water for two hours (72.2% elongation), and is a suitable material for molding into a soft contact lens. A disk molded from this product and immersed in methanol for 2 hours at room temperature will increase in weight 313% (75.2% elongation). The crosslinked nature of the product permits it to swell in water to an equilibrium value. When the product has been boiled in water, cooled and then reboiled, the product contracts when it reaches the boiling point. On cooling, it expands. However, on subsequent boiling and cooling, the product comes back to the same size and shape. The boiling and cooling cycle may be repeated many times. Cast or molded films that are useful as wound dressings and will slowly release sulfadiazine may be prepared from the resin composition of this Example by incorporating in the polyurethane-diallyl phthalate composition sulfadiazine.

EXAMPLE VI

A polyurethane-pentaerythritol triacrylate composition is manufactured by adding to 305.5 parts of the 9.82% hydrophilic polyurethane solution described in Example I above. 4.5 parts of pentaerythritol triacrylate manufactured by Celanese Chemical Company, Dallas, Tex.; and 0.5335 parts of tertiary-butyl peroctoate. The alcohol is removed under vacuum to give a product that is cured at 125° C. for 15 minutes under pressure. The resulting composition had a water uptake of 102% (9.9% elongation), and a methanol uptake of 131% (13.7% elongation).

The composition following removal of the alcohol contains 100 parts of polyurethane and 25 parts of pentaerythritol triacetate. The product may be extruded prior to molding, to form a hydrophilic catheter having desirable physical properties.

EXAMPLE VII

By the procedure described in Example I above, a polyurethane-trimethylol propane trimethacrylate composition is prepared by dissolving 4.5 parts of trimethylol propane trimethacrylate and 0.317 parts of tertiary-butyl peroctoate catalyst in 305.5 parts of 95% ethanol containing 30 parts of the hydrophilic polyurethane resin described in Example I.

The cured resin after molding under pressure for 15 minutes at 150° C. has a water uptake of 393% (64.3 elongation), the methanol uptake is 424% (88.9% elongation).

In the solution of polyurethane-trimethylol propane trimethacrylate in ethanol described above in this Example, may be suspended 3 percent by weight (based on resin solids) of mercurous acetate. This solution can be applied to the hull of a boat and will be cured by the actinic rays of the sun to form an insoluble coating which will decrease drag resistance and inhibit marine growth by the slow release of mercury.

EXAMPLE VIII

Polyethylene glycol having a molecular weight of 1450 (2468.6 parts) is melted and mixed at 60° C. with 324.2 parts of diethylene glycol and 12.3 parts of water. Delta gluconolactone (108.5 parts) and 1626.5 parts of DESMODUR W ® are then dispersed well and added to the mixture of polyols. The reaction mixture is cooled to 50° C. and 5 parts of dibutyl tin dilaurate is added with stirring. When the temperature of the reaction mixture reaches 80° C., it is poured into teflon pans and cured in an oven at 100° C. for 20 minutes. The polymer is removed from the teflon pans, cut into small cubes about 1 cm square, placed in a container with sufficient methanol to cover the resin and permitted to swell for 1 hour. Eight hundred and thirty parts by volume of a 10 percent by weight sodium hydroxide solution is added to the swollen polyurethane cubes and methenol and the mixture is stirred until the polyurethane cubes dissolve. The solution is then adjusted to pH 8.8 with hydrochloric acid. The solution is then filtered and the solids content is determined. To that amount of the solution which contains 200 parts of solids is added 80 parts of diallyl phthalate and 6 parts of tertiary-butyl-perbenzoate catalyst. The solution may be cast as a film and cured in an oven at 135° C. to provide an alcohol insoluble crosslinked hydrophilic film.

Alternatively, the ethanol may be removed from the solution under vacuum at room temperature to provide a white solid that may be extruded at low temperature and then cured by heating for 2 hours at 52° C. to form water and gas permeable tubing useful in kidney dialysis equipment after soluble components, present in the resin have been leached out.

EXAMPLE IX

A polyurethane resin containing polypropylene oxide is prepared by the method described in Example I above by melting together:

| | |
|---|---|
| Polypropylene glycol (m. wt. 2000) | 300 parts |
| Diethylene glycol | 50 parts |

-continued

| DESMODUR W ® | 160 parts | and adding 3 parts by volume of stannous octoate. This polyurethane resin is 25% modified by the addition to the polyurethane solution in ethanol of 127.5 parts of trimethylol propane triacrylate and 11 parts of tertiary-butyl perbenzoate as described in Example III. The cured polyurethane-polyene polymer is similar in molecular weight and physical properties to the product of Example III but is more rigid (being 25% modified) and not hydrophilic (containing a major amount of polypropylene oxide).

EXAMPLE X

To 305 parts of the polyurethane solution in 95% ethanol described in Example I above is added with stirring 4.5 parts of trimethylol propane triacrylate and 0.315 parts of isopropyl percarbonate. The solution is cast onto a release surface and the solvent allowed to evaporate. The film is heated at 125° C. for 45 minutes to form an alcohol insoluble hydrophilic membrane.

What is claimed is:

1. As an article of manufacture, a shaped, three-dimensional structure formed of a hydrophilic polyurethane polyene composition comprising from about 10 to about 50 parts by weight of a polyene selected from the group consisting of polyallyl esters having the formula:

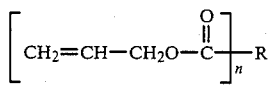

wherein n is a whole number larger than 1 and smaller than 4, and R is the residue of a polybasic acid; and polyacrylic esters having the formula:

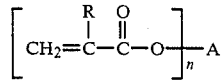

wherein n is a whole number larger than 2 and smaller than 7, R is hydrogen or a methyl radical and A is the residue of a polyhydric alcohol; and about 100 parts by weight of a hydrophilic polyurethane resin.

2. The article of manufacture as defined in claim 1 wherein the structure is a film.

3. The article of manufacture as defined in claim 2 wherein the film contains a medicament.

4. The article of manufacture as defined in claim 1 wherein the structure is a burn dressing in the form of a film.

5. The article of manufacture as defined in claim 1 wherein the structure is in the form of an implant containing a medicament.

6. The article of manufacture as defined in claim 5 wherein the medicament is a hormone.

7. The article of manufacture as defined in claim 5 wherein the medicament is a steroid.

8. The article of manufacture as defined in claim 1 wherein the structure is in the form of an intrauterine device.

9. The article of manufacture as defined in claim 8 wherein the intrauterine device contains a contraceptive composition.

10. The article of manufacture as defined in claim 9 wherein the contraceptive is lactic acid.

11. The article of manufacture as defined in claim 1 wherein the structure is in the form of a diaphragm.

12. The article of manufacture as defined in claim 1 wherein the structure is in the form of a canula.

13. The article of manufacture as defined in claim 12 wherein the canula has distributed throughout its mass is a medicament.

14. The article of manufacture as defined in claim 1 wherein the structure is in the form of an oral delivery system containing a pharmacologically active agent.

15. The article of manufacture as defined in claim 1 wherein the structure is in the form of a gas permeable membrane.

16. The article of manufacture as defined in claim 1 wherein the structure is in the form of a moisture-vapor permeable membrane.

17. The article of manufacture as defined in claim 1 wherein the structure has been molded.

18. The article of manufacture as defined in claim 1 wherein the structure is a contact lens.

19. The article of manufacture as defined in claim 18 wherein the structure is cast into the form of a contact lens.

20. The article of manufacture as defined in claim 1 wherein the structure is a corneal prosthesis.

21. The article of manufacture as defined in claim 1 wherein the structure is a surgical drape in the form of a film.

22. The article of manufacture as defined in claim 21 wherein the film is coated on at least one side with an adhesive.

23. The article of manufacture as defined in claim 1 wherein the structure is in the form of a dialysis membrane.

* * * * *